| United States Patent [19] | [11] | 4,082,813 |
|---|---|---|
| Toth et al. | [45] | Apr. 4, 1978 |

[54] 3-IODA-α-ETHYNYL BENZHYDROL

[75] Inventors: Edit Toth; Jozsef Törley Sandor Gorög; Laszlo Szporny; Eva Palosi; Szabolcz Szeberenyi, all of Budapest, Hungary

[73] Assignee: Richter Gedeon Vegyeszeti Gyar Rt., Budapest, Hungary

[21] Appl. No.: 630,512

[22] Filed: Nov. 10, 1975

Related U.S. Application Data

[62] Division of Ser. No. 495,846, Aug. 8, 1974, Pat. No. 3,965,179.

[30] Foreign Application Priority Data

Aug. 15, 1973 Hungary .............................. RI 520

[51] Int. Cl.² ............................................... C07C 33/06
[52] U.S. Cl. .................................. 260/618 B; 71/122; 260/558 A; 260/590 R; 260/590 C; 260/592; 260/612 D; 260/618 E
[58] Field of Search ..................................... 260/618 B

[56] References Cited

U.S. PATENT DOCUMENTS 2,711,384  6/1955  Darley .............................. 260/618 B

OTHER PUBLICATIONS

Dillard et al., "J. Med. Chem.," 10(1), 40–42 (1966).
Purcell et al., "J. Med. Chem.," 11(2), 199–203 (1968).
Cadiot, "Ann Chim (France) 1, 214–229 (1956).
Rauss–Godineau et al., "Bull. Soc. Chim. France," 1966 (9), 2885–2892.

Primary Examiner—Norman Morgenstern
Attorney, Agent, or Firm—Karl F. Ross

[57] ABSTRACT

The invention is directed to a new substituted derivative of α-ethynyl-benzophenone, namely, the 3-iodo-α-ethynyl-benzhydrol which has high antifungal activity.

1 Claim, No Drawings

3-IODA-α-ETHYNYL BENZHYDROL

The invention relates to a process for the preparation of α-ethynyl benzophenones and ring-substituted derivatives thereof, by reacting the corresponding benzophenones with acetylene. The essential feature of the invention is that the reacting of starting benzophenones with acetone is carried out at atmospheric pressure, at ambient temperature in an aprotic solvent, in the presence of a tertiary alcohol of an alkali metal.

The literature describes several processes for converting benzophenone and substituted derivatives thereof into the corresponding α-ethynyl derivatives. The practical performance of these known processes presents, however, many difficulties. The yields are low in consequence of the formation of by-products; the technological procedure is complicated and long reaction times are necessary to obtain satisfactory grades of conversion.

In a known process, benzophenone is reacted with ethynylene-magnesium bromide (Br—Mg—C≡C—Mg—Br) in the presence of ethyl alcohol (V. K. Teterin and A. P. Ivanov: J. Gen. Chem. USSR. 7, 1629 1937); in this way tetraphenyl butyne diol is formed as by-product beside the desired ethynyl benzophenone. In addition to the difficulties of isolation and low yields (50 to 60 percent) a further drawback of this process is that it is performed in a multiplity of steps: ethyl magnesium bromide is formed first, by reacting magnesium with ethyl bromide; acetylene gas is then introduced into the anhydrous ether solution of the ethyl magnesium bromide until the evolution ethane gas, and the thus obtained ethynylene magnesium bromide is reacted finally with the benzophenone.

According to an other known method (German Patent Specification No. 1 028 561; USA Patent Specification No. 2 957 006) liquid ammonia is cooled by the aid of a mixture of acetone and dry ice to a temperature between −60° C and −70° C; acetylene gas is then introduced into the cooled liquid ammonia, while metallic sodium or potassium is added in minor portions to the reaction mixture. Thereafter, a solution of the benzophenone in anhydrous ether is introduced slowly into the obtained heterogenic reaction mixture. After the end of the reaction, the liquid ammonia is left to evaporate overnight. The obtained reaction mixture is decomposed with an acid; the desired product is isolated by extraction with ether and then purified further. This process has drawback that the use of a special equipment is requested for the performance thereof, the process is to be performed at very low temperature and the technological procedure is extremely dangerous.

There have been described also processes, wherein potassium hydroxide was used for the formation of the alkali metal acetylide. According to a specific performance of these processes the potassium hydroxide is used in the form of an anhydrous powder, prepared by furing potassium hydroxide in a nickel cup at high temperature, cooling the melt, grinding and sieving the cake to a fine powder. The thus prepared pulverized potassium is used in a great excess for performing the reaction, in order to shift the reaction equilibrium into the desired direction. This preparation of the potassium hydroxide condensing agent is difficult and requires a multiplity of operations; the very hydroscopic potassium hydroxide must be handled carefully; all these factors are serious drawbacks in the commercial performance of the process. A further disadvantage is the fact that the required great excess of the potassium hydroxide causes harmful side reactions, polymerization and forming acetylene glycols (A. J. Zekharova: J. Gen. Chem. USSR., 11, 939 (1941); P. Cadiot: Bull. Soc. Chim. France 1951, 100; P. Cadiot: Ann. Chim. (13) 1, 214 (1956); J. Godineau, P. Cadiot: Bull. Soc. Chim. France 9 2885 (1966).

According to an other method of performing the process using potassium hydroxide, the reaction is carried out in a solvent mixture containing primary alcohols. The corresponding ethynyl derivative is obtained at atmospheric pressure with yields of 57–76 %; the ethynyl-content of the product is between 83 % and 95 %. To obtain a product of satisfactory purity, further purification operations must be carried out, whereby the yield is reduced still further. The yield can be increased by working at elevated pressures, but the necessity of pressure-proof equipment and dangerousness of the working with acetylene at higher pressures are serious drawbacks also in this case (I. N. Nazarov et al.: Invest. Akad. Nank SSSR., Otdel. Khim. Nank, 1370 (1956); N. N. Libman et al.: Khim Pharm. Zh. 1 (3), 31 (1967).

Japanese inventors used lithium acetylide or an ethylene diamine complex thereof for the ethynylating of benzophenones. Very low yields of 40 % to 67% were obtained by this process (Hauro Saikachi, Tokujiro Kitegava: Yakugaku Zasshi 89 (11) 1626 (1969).

All the above mentioned drawbacks are completely eliminated by the process of the present invention. It has been found that the conversion of the benzophenones into the corresponding α-ethynyl derivatives can be carried out in short time with high yields, at atmospheric pressure, without formation of by-products if the starting benzophenone is reacted with acetone in the presence of a tertiary alcoholate of an alkali metal, in a solvent delivering no protons to the reactants.

The new process of the present invention has the advantage over the known processes outlined above that it is a simple technological procedure which can be easily performed on a commercial scale. There is no need to use liquid ammonia; the reaction is carried out at atmospheric pressure, and no special equipment is needed to its performance. As a further advantage, the benzophenones can be converted with practically quantitative yield into the corresponding ethynyl derivatives. These are obtained in a high purity grade, so that no special purification processes as chromatography, are needed. Another advantage is that also benzophenones containing nitro or amino groups as substituent can be ethynylated with high yields (84 to 90 %), while the known processes give in such cases only yields between 40 % and 70 %.

According to the present invention, the ethynylating of benzophenones is carried out by reacting the benzophenone starting material with acetylene at atmospheric pressure, in the presence of an alkali metal tertiary alcoholate, in a solvent medium delivering no protons.

As alkali metal tertiary alcoholates, especially potassium tertiary alcoholates as potassium tert.-amylate or preferably potassium tert.-butylate may be used.

As solvent medium delivering no protons, e.g. benzene, toluene, xylene, N,N-dimethyl formamide, N-methyl acetamide, N-methyl pyrrolidone, dimethyl sulphoxide, 1,2-dimethoxy ethane, diethyl ether, dioxane or tetrahydrofuran can be used in the process of the invention. The reaction is carried out preferably in tetrahydrofuran as solvent medium at a temperature between −20° C and +40° C, preferably at 20°-25° C.

The practical performance of the process of the invention can be accomplished preferably in the following way:

Potassium tert.-butylate or tert.-amylate is dissolved within a few minutes in tetrahydrofuran, at room temperature in a nitrogen atmosphere and then acetylene gas is passed through the solution at room temperature, for 30 to 60 minutes. The starting benzophenone, or preferably a tetrahydrofuran solution thereof is then added to the reaction mixture, while the stream of acetylene gas is passed further through the reaction mixture. The practically quantitative completion of the ethynylation reaction requires 15 to 60 minutes, depending on the used starting materials. The procedure can be monitored easily by thin layer chromatography. Thereafter the reaction mixture is decomposed by adding a dilute acid or an aqueous solution of ammonium chloride, and the tetrahydrofuran is distilled off. The residual ethynylated benzophenone is recovered from the aqueous phase by filtration or by solvent extraction. The obtained crude product may be purified, if needed, by recrystallization or by distillation.

The new process of the invention can be used favourably for the preparation of new substituted derivatives of α-ethynyl-benzophenone not described hitherto in the literature. These new products, e.g. the compounds described in the Examples 1 to 10, show valuable pharmacological properties; they exert a blocking or inducing effect, respectively, on the microsomal enzyme system of the liver and have also antiviral and fungicidal effects. Furthermore, these new compounds are valuable starting materials in the synthesis of other biologically active compounds.

The invention is elucidated in detail by the aid of the following non-limiting Examples.

EXAMPLE 1

Acetylene is bubbled through a stirred solution of 146 g. of potassium-tert.butylate in 584 ml. of tetrahydrofuran for 30 minutes at room temperature. Thereafter a solution of 297.4 g. of 4-(β-diethylaminoethoxy)-benzophenone in 300 ml. of tetrahydrofuran is added to the mixture and the introduction of acetylene is continued at room temperature. As evidenced by thin layer chromatography, the reaction proceeds quantitatively within 30 minutes. The reaction mixture is decomposed with an aqueous solution of ammonium chloride, tetrahydrofuran is distilled off in vacuo, and the product is extracted with benzene. The benzene phase is washed until neutral, dried over anhydrous magnesium sulfate, and evaporated to dryness in vacuo. 318.6 g. (98.5 %) of 4-(β-diethylaminoethoxy)-α-ethynylbenzohydrol, a new compound not described in the literature so far, are obtained. M.p.: 87°-88° C.

Analysis for $C_{21}H_{25}NO_2$: Calculated: C 77.98 %, H 7.79 %, N 4.33 %; Found: C 78.05 %, H 7.60 %, N 4.40 %.

EXAMPLE 2

Acetylene is introduced into a solution of 150 g. of potassium-tert.amylate in 900 ml. of tetrahydrofuran for 30 minutes at 30° to 22° C, and then 300 g. of 3-iodobenzophenone are added to the mixture. The introduction of acetylene is continued at 20° to 22° C for further 45 minutes, thereafter the mixture is neutralized with 5 n hydrochloric acid under a nitrogen atmosphere. The organic phase is separated, dried over anhydrous sodium sulfate, and the solvent is distilled off in vacuo. 316.7 g. (97.3 %) of 3-iodo-α-ethynyl-benzhydrol, a new compound not described in the literature, are obtained. B.p.: 138°-139° C/0.1 mmHg.

Analysis for $C_{15}H_{11}IO$:
Calculated: C 53.91 %, H 3.32 %, I 37.98 %, Found: C 54.01 %, H 3.08 %, I 38.04 %.

EXAMPLE 3

Acetylene is bubbled through a stirred mixture of 147 g. of potassium-tert.butylate and 600 ml. of tetrahydrofuran for 30 minutes at 20° to 22° C, thereafter a solution of 210 g. of 2,5-dimethyl-benzophenone in 240 ml. of tetrahydrofuran is added to the reaction mixture within 20 minutes. The introduction of acetylene is continued for further 20 minutes, then the reaction mixture is decomposed with an aqueous solution of ammonium chloride. Tetrahydrofuran is distilled off in vacuo, and the separated product is extracted into methylene chloride. The methylene chloride phase is washed until neutral, dried over anhydrous magnesium sulfate, and the solvent is distilled off in vacuo. 231.4 g. (97.8 %) of 2,5-dimethyl-α-ethynyl-benzhydrol, a new compound not described in the literature, are obtained. B.p.: 119°-120° C/0.05 mmHg.

Analysis for $C_{17}H_{16}O$: Calculated: C 86.40 %, H 6.83 %, Found: C 86.29 %, H 7.01 %.

EXAMPLE 4

Acetylene is bubbled through a stirred mixture of 73 g. of potassium-tert.butylate and 300 ml. of tetrahydrofuran for 30 minutes at 20° to 22° C, thereafter a solution of 119.2 g. of 4-n-butyl-benzophenone in 150 ml. of tetrahydrofuran is added to the reaction mixture within 15 minutes. The introduction of acetylene is continued for 15 minutes, thereafter the reaction mixture is decomposed with 5 n hydrochloric acid, tetrahydrofuran is distilled off in vacuo, and replaced by water. The product is extracted into methylene chloride. The organic phase is washed until neutral, dried over anhydrous magnesium sulfate, and the solvent is distilled off in vacuo. 127.8 g. (96.7 %) of 4-n-butyl-α-ethynyl-benzhydrol, a new compound not described in the literature, are obtained. B.p.: 146° C/0.2 mmHg.

Analysis for $C_{19}H_{20}O$: Calculated: C 86.32 %, H 7.63 %, Found: C 86.38 %, H 7.51 %.

EXAMPLE 5

Acetylene is bubbled through a stirred mixture of 84 g. of potassium-tert.butylate and 500 ml. of tetrahydrofuran for 30 minutes at 30° to 22° C, thereafter 106 g. of 2-methoxy-benzophenone are added. The introduction of acetylene is continued for 60 minutes. The reaction mixture is processed as described in Example 3. 114.8 g. (96.4 %) of 2-methoxy-α-ethynyl-benzhydrol, a new compound not described in the literature, are obtained. M.p.: 69° C.

Analysis for $C_{16}H_{14}O_2$: Calculated: C 80.64 %, H 5.92 %; Found: C 80.71 %, H 5.68 %.

EXAMPLE 6

Acetylene is introduced into a stirred mixture of 56 g. of potassium tert.-butylate and 220 ml. of tetrahydrofuran for 30 minutes at 20° to 22° C, thereafter a tetrahydrofuran solution of 68 g. of 3,4,5-trimethoxy-benzophenone is added to the reaction mixture within 15 minutes. The introduction of acetylene is continued for 30 minutes, then the reaction mixture is processed as described in Example 3. 70.9 g. (95 %) of 3,4,5-trimethoxy-α-ethynyl benzhydrol, a new compound not described in the literature, are obtained. M.p.: 88° C.

Analysis for $C_{18}H_{18}O_4$: Calculated: C 72.46 %, H 6.08 %; Found: C 75.52 %, H 6.01 %.

EXAMPLE 7

2,4-Dimethoxy-α-ethynyl-benzhydrol, a new compound not described in the literature, is obtained with a yield of 94 % by ethynylating 2,4-dimethoxy-benzophenone as described in Example 6. The boiling point of the product is 148°–150° C/0.08 mmHg.

Analysis for $C_{17}H_{16}O_3$: Calculated: C 76.10 %, H 6.01 %; Found: C 75.93 %, H 6.30 %.

EXAMPLE 8

Acetylene is introduced into a stirred mixture of 84 g. of potassium-tert.-butylate and 330 ml. of tetrahydrofuran for 30 minutes at 20° to 22° C, thereafter a tetrahydrofuran solution of 60.55 g. of 3-nitro-4-aminobenzophenone is added to the reaction mixture within 15 minutes. The introduction of acetylene is continued for 30 minutes, thereafter the reaction mixture is processed as described in Example 3. 58.3 g. (87 %) of 3-nitro-4-amino-α-ethynyl-benzhydrol, a new compound not described in the literature, are obtained. M.p.: 91°–92° C.

Analysis for $C_{15}H_{12}N_2O_3$: Calculated: C 67.15 %, H 4.51 %, N 10.44 %; Found: C 67.30 %, H 4.23 %, N 10.50 %.

EXAMPLE 9

2-Benzoylamino-5-chloro-benzophenone is ethynylated as described in Example 6 to give the new product 2-benzoylamino-5-chloro-α-ethynyl-benzhydrol with a yield of 84 %. The product melts at 178°–179° C.

Analysis for $C_{22}H_{16}ClNO_2$: Calculated: C 73.03 %, H 4.46 %, Cl 9.80 %, N 3.87 %; Found: C 72.98 %, H 4.19 %, Cl 9.95 %, N 3.90 %.

EXAMPLE 10

3-Nitro-4-chloro-α-ethynyl-benzophenone, a new compound not described in the literature, is prepared with a yield of 92 % by ethynylating 3-nitro-4-chlorobenzophenone as described in Example 6. The boiling point of the product is 178°–179° C/0.15 mmHg.

Analysis for $C_{15}H_{10}ClNO_3$: Calculated: C 62.62 %, H 3.50 %, Cl 12.32 %, N 4.87 %; Found: C 62.70 %, H 3.28 %, Cl 12.30 %, N 4.90 %.

EXAMPLE 11

Acetylene is bubbled through a stirred mixture of 147 g. of potassium-tert.butylate and 600 ml. of tetrahydrofuran at room temperature (20° to 22° C), thereafter a solution of 251 g. of 2,4-dichloro-benzophenone in 400 ml. of tetrahydrofuran is added within 30 minutes. The introduction of acetylene is continued additional 20 minutes. The reaction mixture is processed as described in Example 3 to yield 260.4 g. (94 %) of 2,4-dichloro-α-ethynyl-benzhydrol. M.p.: 75° C.

Analysis for $C_{15}H_{10}Cl_2O$: Calculated: C 65.00 %, H 3.64 %, Cl 25.59 %; Found: C 64.85 %, H 3.92 %, Cl 25.70 %.

EXAMPLE 12

3,4-Dichloro-benzophenone is ethynylated as described in Example 11 to give 3,4-dichloro-α-ethynyl-benzhydrol with a yield of 96 %. The boiling point of the product is 135° C/0.1 mmHg.

Analysis for $C_{15}H_{10}Cl_2O$: Calculated: C 65.00 %, H 3.64 %, Cl 25.59 %; Found: C 65.12 %, H 3.51 %, Cl 25.60 %.

EXAMPLE 13

4,4'-Dichloro-benzophenone is ethynylated as described in Example 11 to give 4,4'-dichloro-α-ethynyl-benzhydrol with a yield of 92 %. The product melts at 73°–74° C.

Analysis for $C_{15}H_{10}Cl_2O$: Calculated: C65.00 %, H 3.64 %, Cl 25.59 %; Found: C 65.08 %, H 3.51 %, Cl 25.55 %.

EXAMPLE 14

3-Chloro-benzophenone is ethynylated as described in Example 11 to give 3-chloro-α-ethynyl-benzhydrol with a yield of 94.7 %. The boiling point of the product is 120°–122° C/0.1 mmHg.

Analysis for $C_{15}H_{11}ClO$: Calculated: C 74.23 %, H 4.57 %, Cl 14.61 %; Found: C 74.28 %, H 4.70 %, Cl 14.51 %.

EXAMPLE 15

4-Bromo-benzophenone is ethynylated as described in Example 11 to give 4-bromo-α-ethynyl-benzhydrol with a yield of 96 %. The product melts at 80°–81° C.

Analysis for $C_{15}H_{11}BrO$: Calculated: C 62.74 %, H 3.86 %, Br 27.83 %; Found: C 62.58 %, H 3.99 %, Br 27.81 %.

EXAMPLE 16

Acetylene is introduced for 30 minutes into a 20°–22° C mixture of 118 ml. of tetrahydrofuran and 16.8 g. of potassium-tert.butylate, and thereafter 22.7 g. of 4-nitrobenzophenone are added to the mixture. The introduction of acetylene is continued at 20° to 22° C for an additional 30 minutes, then the mixture is neutralized with 5 n hydrochloric acid under nitrogen atmosphere. The organic phase is separated, dried over anhydrous sodium sulfate, and the solvent is distilled off in vacuo. 23.1 g. (91 %) of 4-nitro-α-ethynyl-benzhydrol are obtained; m.p.: 88°–89° C.

Analysis for $C_{15}H_{11}NO_3$: Calculated: C 71.14 %, H 4.37 %, N 5.53 %; Found: C 71.28 %, H 4.51 %, N 5.44 %.

What we claim is:

1. 3-iodo-α-ethynyl-benzyhydrol.

* * * * *